United States Patent [19]

Wu et al.

[11] Patent Number: 4,687,676

[45] Date of Patent: Aug. 18, 1987

[54] RUMEN-STABLE PELLETS

[75] Inventors: Stephen H. Wu; Mohammad A. Sandhu, both of Kingsport, Tenn.

[73] Assignee: Eastman Kodak Company, Rochester, N.Y.

[21] Appl. No.: 848,439

[22] Filed: Apr. 7, 1986

Related U.S. Application Data

[60] Division of Ser. No. 689,405, Jan. 7, 1985, Pat. No. 4,595,584, which is a continuation of Ser. No. 498,446, May 26, 1983, abandoned, which is a continuation-in-part of Ser. No. 397,314, Jul. 12, 1982, abandoned.

[51] Int. Cl.$^4$ .......................... A61K 9/22; B02C 17/00
[52] U.S. Cl. ........................................... 427/3; 241/15; 241/16; 241/26; 106/290; 106/308 R; 106/308 F; 106/308 M; 524/904; 604/890
[58] Field of Search ............... 524/904; 241/15, 16, 241/26; 106/290, 308 R, 308 F, 308 M; 604/890; 427/3

[56] References Cited

U.S. PATENT DOCUMENTS

| | | | |
|---|---|---|---|
| 3,981,984 | 9/1976 | Signorino | 106/190 |
| 4,003,872 | 1/1977 | Rolles et al. | 524/904 |
| 4,181,708 | 1/1980 | Dannelly | 424/419 |
| 4,181,709 | 1/1980 | Dannelly | 424/19 |
| 4,236,934 | 12/1980 | Bell | 241/16 |
| 4,278,576 | 7/1981 | Goldman | 524/904 |
| 4,285,994 | 8/1981 | Pearce et al. | 524/904 |
| 4,318,747 | 3/1982 | Ishijima et al. | 241/16 |
| 4,469,282 | 9/1984 | Booz | 241/16 |
| 4,481,328 | 11/1984 | Harréus et al. | 524/904 |
| 4,484,951 | 11/1984 | Uchimura et al. | 241/16 |
| 4,595,584 | 6/1986 | Wu et al. | 424/19 |

FOREIGN PATENT DOCUMENTS

| | | | |
|---|---|---|---|
| 56-5588 | 2/1981 | Japan | 241/16 |
| 872149 | 7/1961 | United Kingdom | |

OTHER PUBLICATIONS

Chemical Abstracts: vol. 89, No. 18, Oct. 1978, abstract 89:147656q.

Primary Examiner—Ronald W. Griffin
Attorney, Agent, or Firm—John F. Stevens; William P. Heath, Jr.

[57] ABSTRACT

Disclosed is a composition adapted for use in coating pellets orally administrable to ruminants which protects the core material in the rumen and releases it in the abomasum comprising a film-forming polymeric material, a hydrophobic material dispersed in said polymeric material, and a physiologically acceptable flake material dispersed in said polymeric material, the flake material having been treated by bringing the particles into rubbing contact with the hydrophobic material so that the surface of the particles of flake material become hydrophobic.

3 Claims, No Drawings

RUMEN-STABLE PELLETS

DESCRIPTION

This is a divisional of application Ser. No. 689,405, filed Jan. 7 1985 now U.S. Pat. No. 4,595,584, issued June 17, 1986, which is a continuation of Ser. No. 498,446, filed May 26, 1983, now abandoned, which in a continuation-in-part of Ser. No. 397,314, filed July 12, 1982, now abandoned.

TECHNICAL FIELD

This invention relates in genereal to pellets adapted to be orally administered to ruminants and which are beneficial to ruminants after passing the rumen and reaching the abomasum and/or intestines. More particularly, this invention relates to pellets having, in terms of structure, a core material such as a nutrient or medicament, and a coating over the core material which protects the core in the environment of the rumen, but which loses continuity under the more acidic conditions of the abomasum to render the core material available for utilization by the animal.

BACKGROUND ART

In ruminants, e.g., beef and dairy cattle, sheep, etc., ingested feed first passes into the rumen, where it is pre-digested by fermentation. During this period of fermentation the ingested feed is subjected to rumination, which is part of a digestive process involving regurgitation. After a period of fermentation, adsorption of digested mutrients starts and continues in the subsequent sections of the digestive tract. This digestive process is described in detail by D. C. Church, "Digestive Physiology and Nutrition of Ruminants," Vol. 1, O.S.U. Book Stores, Inc., of Corvallis, Oreg.

The rumen serves as an important location of metabolic breakdown of ingested foodstuffs through the action of microorganisms which are present therein. Ingested food is typically retained in the rumen for from about 6 to about 30 hours, during which time it is subject to metabolic breakdown by the rumen microorganisms. Much ingested protein material is broken down in the rumen to soluble peptides and amino acids and utilized by the rumen microorganisms. When the rumen contents pass into the abomasum and intestine, the microbial mass is digested, thus providing protein to the ruminant. Thus, the natural nutritional balance of the ruminant animal is primarily a function of the microbial composition and population.

In preparing nutrients and medicaments intended for administration to ruminants, it is important to protect the active ingredients against the environmental conditions of the rumen, i.e., microbial degradation and the effects of a pH in the range of about 5.5 to about 7.0, so the active substance will be saved until it reaches the particular location where adsorption takes place. It is well known that the rate of meat, wool and/or milk production can be increased if sources of growth limiting essential amino acids, and/or medicaments, are protected from alteration by microorganisms residing in the rumen and become available for direct adsorption by the animal later in the gastrointestinal tract.

Materials which protect the core against degradation by the rumen contents should be resistant to attack by the rumen fluid which contains enzymes or microorganisms but must make the active ingredient available rapidly in the more acidic fluid of the abomasum at a pH within the normal physiological range of about 2 to about 3.5.

Because proteins are subject to breakdown in the rumen, it has been suggested that protein-containing nutrients fed to ruminants be treated so as to permit passage without microbial breakdown through the rumen to the abomasum. Suggested procedures have included coating the protein materal, for example, with fats and vegetable oils; heat treating of the protein material; reacting the protein material with various compounds such as formaldehyde, acetylenic esters, polymerized unsaturated carboxylic acid or anhydrides and phosphonitrilic halides, etc.

It is well known that all proteins found in animal and plant life are chemical compounds containing different combinations of over 20 amino acids, the number and arrangement of such acids being fixed in any particular protein. Twelve of these amino acids can be synthesized in nutritionally adequate amounts from other substances by biochemical processes normally present in most animals, but the remaining 10 amino acids are not synthesized in sufficient quantities and must be ingested by the animal. Since the proportions of the constituent amino acids in a particular protein cannot be varied, the essential amino acid least in supply limits the amount of that protein which can be produced by the animal. Consequently, for any given diet, there will be a particular essential amino acid which limits the production of protein incorporating that essential amino acid unless, of course, two or more such amino acids are equally limiting.

It is likewise well-known that medicaments are more effective when they are protected from the environment of the rumen. See, for example, U.S. Pat. Nos. 3,041,243 and 3,697,640.

In accordance with the present invention, a polymeric coating having a hydrophobic substance and a flake material dispersed therein, which is resistant to environmental conditions of the rumen but releases the core material under the environmental conditions of the abomasum (postruminal), provides a very desirable utilization efficiency by ruminants. The core material may also contain a neutralizer to provide a pH above about 5.5.

The coating material has the ability to withstand environmental conditions of the rumen, and the ability to expose the core material of the pellet in the environment of the abomasum. Thus, the coating material is resistant to pH conditions of about 5.5 for at least about 24 hours. The coating material releases the core material upon exposure to postruminal environmental conditions having a pH of about 3.5 after a time of about 10 minutes to about 6 hours. The exposure of the core may occur by the coating becoming permeable to the fluids therein or by dissolving or disintegrating. Another requirement for the coating material is to have the ability to withstand storage conditions of relatively high heat and/or humidity without a significant amount of blocking.

U.S. Patents of interest include Nos. 3,619,200; 3,880,990; 3,041,243; 3,697,640; 3,988,480; 3,383,283; 3,275,518; 3,623,997; 3,073,748; 3,829,564; 3,832;252; 3,917,813.

U.S. Pat. No. 4,181,708, incorporated herein by reference, discloses coatings comprising a polymer, hydrophobic substance and flake material, but does not disclose treatment of the flake material.

Also, U.S. Pat. Nos. 4,177,255; 4,196,187; 4,181,709 and 4,181,710 are of interest.

DISCLOSURE OF INVENTION

The present invention provides an improved rumen protected coating for pellets comprising a filmforming polymeric material, a hydrophobic material, and a flake material. This composition is similar to that disclosed and claimed in U.S. Pat. No. 4,181,708, except in this invention, improved results are obtained by a special treatment of the flake material, (e.g. talc), by bringing the flake material in rubbing contact with the hydrophobic material (e.g., stearic acid). It has been found that rumen protection can be substantially improved by this special treatment of the flake material.

According to the present invention, the flake material is treated by bringing the particles thereof into rubbing contact with the hydrophobic material, preferably in a liquid medium, for a sufficient time to cause the flake material to become more hydrophobic. Generally, from about 2 to about 28 hours under at least light shearing stress and/or direct pressure (about 0.1 to about 20 Kg/cm$^2$) is sufficient. In this manner, it is believed that the surface energy of the flake material is changed such that it becomes more hydrophobic.

To cause the rubbing contact between the flake material and the hydrophobic material, it is preferred that they be ball-milled. However, other conventional processes and equipment can be used. For example, other milling processes, grinding, vigorous mixing, and the like may be used. Vehicles, such as mineral spirits, volatile hydrocarbons and ketones, may be used to disperse the hydrophobic material and flake material if desired.

A preferred ball mill used in the practice of this invention comprises a cylindrical container mounted horizontally and partially filled with ceramic balls. The surface modification of the flake material with hydrophobic substances in acetone is accomplished by rotating the ball mill and its contents about the horizontal axis of the mill at a rate sufficient to lift the balls to one side and then cause them to roll, slide, and tumble (cascade) to the lower side.

A laboratory procedure practiced in this invention is described as follows:
1. Weight approximately 570 g of ceramic balls and add these balls into a ball mill. The total volume of the balls is approximately 15-25% of the volume of the cylindrical container.
2. Add 137 g of a mixture of flake material and hydrophobic substance, and 320 mL acetone to the ball mill, and seal the container to minimize evaporation of acetone during the operation.
3. Rotate the ball mill on a roller at a speed of ~90 rpm for about 16 hrs.
4. Decant the contents and wash the container and balls with acetone. The dispersion is ready to be used for the preparation of a coating dope, or the dispersion is dried by evaporation acetone at 50° C. The dry mixture of flake material/hydrophobic substance is then redispersed into a polymer solution to make a coating dope.

The pellets according to this invention are adapted for oral administration to ruminants. The pellets are of a suitable size, such as between No. 10 and No. 18 of U.S. Standard Sieve Size. Also, the pellets must be of suitable density, i.e., a specific gravity of between about 1 and 1.4, have acceptable odor, taste, feel, etc. The pellets include a core and a continuous, film or coating completely encapsulating the core. The pellets are preferably cylindrical, having a diameter of about 1.0–2.0 mm and a length-to-diameter ratio of about 1–2.0:1, or spherical, having a diameter of about 1.0–3.0 mm.

The core is of a material beneficial to the ruminant upon passing the rumen and reaching the abomasum and/or intestine. Normally, the core is a solid material which has been formed into particles, such as by pelletizing. The core should have sufficient body or consistency to remain intact during handling, particularly during the coating operation. Suitable core materials include various medicaments and nutrients such as, for example, antibiotics, relaxants, drugs, anti-parasites, amino acids, proteins, sugars, carbohydrates, etc. The core may also contain inert filler material such as clay.

Some amino acids are suitable for use as a core material, their pH and solubility being as follows:

| Amino Acids Solubility, pI (pH at Isoelectric Point) and pH of Saturated Aqueous Solutions | | | | | |
|---|---|---|---|---|---|
| | Solubility, g/100 g. Water at Temp. | | | | |
| | 0° C. | 25° C. | 50° C. | pI | pH |
| L, or DL-alanine | 12.1 | 16.7 | 23.1 | 6.01 | 5.5–7.0 |
| L-arginine | 8.3 | 21.6 | 40.0 | 11.15 | 10.5–12.5 |
| L-arginine.HCl | 45.0 | 90.0 | 146.0 | — | 5.5–6.0 |
| L-cystine | 0.005 | 0.011 | 0.024 | 5.03 | 5.0–7.0 |
| L-Histidine.HCl | 29.1 | 39.5 | 50.1 | 7.47 (free base) | 3.0–4.5 |
| L-isoleucine | 3.79 | 4.12 | 4.82 | 5.94 | 5.5–7.0 |
| L-Leucine | 2.27 | 2.43 | 2.66 | 5.98 | 5.5–7.0 |
| L-Lysine.HCl | 53.6 | 72.0 | 111.5 | 9.59 | 5.0–6.0 |
| DL-Methionine | 1.82 | 3.38 | 6.07 | 5.74 | 5.5–6.5 |
| L-Methionine | 3.0 | 5.14 | 7.4 | 5.74 | 5.5–6.5 |
| L-Ornithine.HCl | 45.0 | 57.0 | 75.0 | 9.70 (free base) | 4.5–6.5 |
| L-Phenylalanine | 1.98 | 2.97 | 4.43 | 5.48 | 5.0–6.0 |
| L-Threonine | 7.0 | 9.5 | 14.0 | 5.64 | 5.0–6.5 |
| L-Tryptophan | 0.82 | 1.14 | 1.71 | 5.89 | 5.5–7.0 |
| L-Valine | 8.34 | 8.85 | 9.62 | 5.96 | 5.5–7.0 |

Other suitable active core materials include glucose, bacitracin, thyrotropin releasing factor and inositol. Proteins from various sources are valuable for practice of the invention. Generally, proteins are polymers derived from various combinations of amino acids. Proteins are amphoteric substances which are soluble or suspendable in aqueous media.

The core material may be made ready for coating by the following method. The nutrient, medicament, or the like, and core neutralizer, if used, are mixed with water, binders, a basic substance for adjusting the core pH, and sometimes inert inorganic substances added to adjust the specific gravity of the pellet and the resulting plastic dough-like mass is extruded or rolled to obtain suitable size particles. Adhesive binders are added to strengthen the pellet and can be nontoxic vegetable gums, starches, cellulose derivatives, animal gums and other similar substances well known in the art of food thickening and tablet making. Inorganic additives used to adjust the specific gravity of the pellet include such substances as insoluble, nontoxic pigment-like materials such as metal sulfates, oxides and carbonates having a relatively high density. After creating suitable size pellets by extrusion, rolling or other suitable means, the pellets are dried to remove the water. The pellets are then coated by contacting them with a solution of the protective coating material in a suitable solvent or mixture of solvents as hereinafter described. Typical solvents of value include lower alcohols, ketones, esters, hyrocarbons, and chlorinated hydrocarbons.

Core materials may be raised in pH to a predetermined degree by mixing a basic neutralization substance therewith or by coating the core with a basic neutralization substance. The acidity is modified by adding nontoxic, insoluble, basic substances such as alkaline earth oxides, hydroxides, or carbonates, to the core material before the pellets forming step. Basic compounds of aluminum such as the various forms of hydrated alumina, aluminum hydroxide, and dibasic aluminum salts of organic acids, having less than 6 carbon atoms, such as dibasic aluminum acetate may also be used. These basic substances are added to the pellets by mixing the core material, basic substance, and binders as described above before adding water. The amount used depends on both the solubility and relative acidic nature of the proteinaceous substance, on the coating composition used to obtain rumen protection and on the thickness of the coating applied. The amount of basic substance used is that quantity which will theoretically neutralize or raise the pH at least to 5.5, preferably to about 7.

The coating material is capable of forming a continuous film around the core by the evaporation of solvent from the coating material. The coating material should be resistant to pH conditions of greater than about 5 for from about 6 to about 30 hours. The coating material should release the core material after exposure to abomasum environmental conditions having a pH of about 2 to about 3.3. Release should occur within the residence time in the abomasum or later in the intestinal track but at least within a time period of 6 hours after contacting pH 3.5 or less. The exposure of the core may occur by the coating becoming permeable to the contents of the rumen, such as by dissolving, disintegrating, or extensive swelling. The coating material is physiologically acceptable, i.e., the coating material should not interfere with the ruminants' healthy or normal body functioning.

Another requirement for the coating material is its ability to withstand abrasion in handling and storage conditions of relatively high heat and/or humidity without a significant amount of blocking or sticking. It should have a sticking temperature of greater than about 50° C. Sticking temperature is defined as the temperature at which an applied force of 0.25 kg/cm² for 24 hours causes the coating of pellets to adhere to the coating of adjacent pellets strongly enough to cause rupture of the coating when the pellets are forceably separated. Also, the coating material is preferably soluble or dispersable in organic solvents having boiling points of between about 40° C. and 140° C. to permit conventional coating processes such as spray coating to be used. Particularly suitable solvents include methylene chloride, chloroform, ethanol, methanol, ethyl acetate, acetone, toluene, isopropanol or mixtures of these.

The coating includes a mixture or blend of at least one polymeric substance, at least one hydrophobic substance, and at least one flake material. Generally, the more acidic and more soluble core materials require greater ratios of hydrophobic substance and flake material to polymeric substance, while more basic and less soluble core materials require less ratios of hydrophobic substance and flake material to polymeric substance within the range. The hydrophobic substance and flake material are normally dispersed in the polymeric matrix.

The coating normally contains about 16–87% by weight polymeric material, about 0.5–32% by weight hydrophobic substance and about 7–80% by weight flake material.

The polymeric substances which are useful in the coatings of this invention include those which, in combination with the hydrophobic substance described hereinafter, are physiologically acceptable and resistant to a pH of greater than about 5 but capable or releasing the core of the pellets at a pH of less than about 3.5, at the normal body temperature of ruminants (37° C.). The polymeric substances include polymers, copolymers and mixtures of polymers and/or copolymers having basic amino groups in which the nitrogen content of the polymeric substance is between about 2 and about 14%. The basic amino groups may be of the aliphatic type in which case they will contain from about 2% to about 10% by weight of nitrogen in the basic amino groups. The basic amino groups may also be of the aromatic type in which the basic amino groups are attached directly to the aromatic ring, or are part of the aromatic ring structure in which case they will contain from about 6% to about 14% nitrogen in the basic amino groups. The polymeric substances are macromolecules of sufficient molecular weight to have film-forming properties when the polymer is deposited from a solution and after removal of a solvent, dispersing medium or on cooling from a melt.

Polymeric substances having the characteristics defined herein include certain modified natural polymers, homo- and interpolymers obtained by addition polymerization methods, homoand copolymers obtained by condensation polymerization methods and mixtures thereof. The polymeric material is comprised of at least one polymer, copolymer, or blend of polymers selected from the group consisting of cellulose derivatives such as cellulose propionate morpholinobutyrate; containing addition-type monomeric moieties such as acrylonitrile; vinylated derivatives of pyridine; styrene; methylstyrene; vinyl toluene; esters and amides of methacrylic acid; acrylic acid; such as a dialkylamino ethyl acrylate or methacrylate in which the alkyl group contains from 1 to 6 carbon atoms, polymerizable ethylenically unsaturated aliphatic hydrocarbon monomers such as ethylene, propylene or butadiene; vinyl esters such as vinyl acetate, vinyl propionate or vinyl stearate; vinyl esters such as methyl, ethyl, propyl or stearyl, vinyl substituted heterocyclic ring or condensed ring compounds containing basic nitrogen configurations such as vinyl carbazole, vinyl quinoline, N-vinylpyrrole and 5-vinyl pyrozoline; containing condensation-type polymers wherein a diacid such as phthalic, terephthalic, and succinic are combined with polyfunctional alcohols to form polyesters wherein either the acid or glycol moiety may contain basic nitrogen not reactive in the polymerization process but reactive to variable pH environments and wherein the same or similar diacids may be reacted with polyfunctional amines to form polyamide-type polymers containing basic nitrogen not reacted in the polymerization process; and other basic nitrogen containing polymers such as preformed polymers which have been formed by reacting an existing polymer with a nitrogen containing organic or inorganic moiety such as polybutadiene to which ammonia has been reacted with the remaining double bond. Especially preferred are poly(vinylpyridine), polymeric derivatives of vinylpyridine, and the copolymers of the various isomers and derivatives of vinylpyridine copolymerized with one or more of the above-mentioned addition type monomers.

Also, especially preferred are copolymers of 2-methyl-5-vinylpyridine and styrene, and in particular, the copolymer of about 75-85% by weight 2-methyl-5-vinylpyridine and about 15-25% by weight styrene, as well as the copolymer of 55-65% by weight 2-methyl-5-vinylpyridine and about 35-45% by weight acrylonitrile. Also especially preferred is a copolymer of about 75-85 wt. % 2-vinylpyridine and about 25-15 wt. % styrene. These copolymers are commercially available or may be produced by conventional techniques well known in the art.

Hydrophobic substances which are physiologically acceptable and have the correct degree of compatability with the polymer are commercially available. It is important that the polymer and hydrophobic substance have a degree of compatability to permit the film to remain intact in the rumen environment, but to permit permeation of the abomasal fluid to the core while the pellet is in the abomasum.

A class of hydrophobic substances of value are fatty acids containing from 10 to 32 carbon atoms such as lauric, oleic, stearic, palmitic and linoleic. These substances are well known to be water insoluble due to the long hydrocarbon radical but to react to water due to the polar nature of the carboxyl group. In the selected basic amino group-containing polymers, the carboxyl group of the fatty acid is able to react with the basic nitrogen group to form a weak salt-type linkage. This attachment to the polymer serves to cause the fatty acid to be fixed in the polymer matrix. The hydrophobic hydrocarbon chain of the fatty acid tends to render the matrix water resistant and thereby decreases swelling of the otherwise water susceptible polar film. Both the interior of the matric film and the surface is now water resistant in aqueous environments at pH above about 5.0. However, at pH values below pH 4.5 and especially below about pH 3.5 the affinity of the basic nitrogen group for water and the hydrogen ion overcomes the increased water resistance. The film reacts with the acid environment and loses barrier properties sufficient to allow the core material to escape to the environment.

Polyfunctional carboxylic acids may be derived from natural products or obtained by organic synthesis but the ratio of carboxyl group to hydrophobic organic radical should be at least 1 to 10 based on the molecular weight of the organic radicals. Also included in this class of synthesized organic hydrophobic acids are mono and polyfunctional acids containing silicone or fluorinated carbon groups located at least 4 atoms distant along the molecular chain from the position of the carboxyl group or groups. Also, included in the class of hydrophobic substances are the nontoxic multivalent metallic salts of the above acids such as the stearates, oleates, fatty acid dimerates, and palmitates of aluminum and iron and the calcium, magnesium and zinc salts of the higher molecular weight crystalline analogs of the above acids. When the cation is trivalent as for aluminum and ferric iron, the molar ratio of organic acid to metal ion is 2 to 1 or 3 to 1 and the acid can be any monofunctional organic acid having one carboxyl group and at least 10 carbon atoms in the organic radical attached to the carboxyl group. When the metal ion is divalent such as ferrous iron, calcium, magnesium or zinc the organic acid may be monocarboxylic or polycarboxylic and the ratio of metal ion to non-carboxylic carbon atoms is at least 1 to 26. Natural and synthetic waxes and resins added at levels depending on the degree of hydrophobicity and compatibility in the matrix film are of value in the practice of the invention. Waxes and resins are useful that have a critical surface tension of less than 31 dynes/cm as determined by the Zisman method described in "Contact Angle Wettability and Adhesion," Advances in Chemistry Series No. 43; Edited by Robert F. Gould; published by the Americal Chemical Society; 1963; Chapter 1; and have a solubility in the matrix film of less than 5%. These waxes and resins are dispersed in the film in at least amounts equal to 2 times the solubility and up to 30% of the total weight of the matrix polymer. Typical waxes and resins include beeswax, petroleum wax, dammar, hard manila, phenolic resins and maleated low molecular weight polyhydrocarbons. Also included in the hydrophobic substances are polymers having weight average molecular weights of from 2000 to 1,000,000, a critical surface tension of less than 31 dynes/cm measured by methods in the reference to Zisman described above. Useful polymers have a solubility or compatability in the matrix film of less than 5% on a weight basis and are present in the film at levels at least equal to two times the solubility and up to 30 weight percent of the matrix film. Of particular value are the polymers and copolymers containing silicone groups in the main polymer chain or in a side chain and polymers and copolymers containing flourinated carbon groups in a side chain. Regardless of the exact nature of the hydrophobic substance it must be soluble or colloidally dispersible in the coating solvent when one is used. The hydrophobic substance makes up from 1 to about 50% of the combined weight of polymeric material and hydrophobic substance.

Suitable hydrophobic substances also include fatty acids having from 12 to 32 carbon atoms, such as oleic acid and stearic acid, dimer acids, timer acids, aluminum salts of fatty acids, waxes, resins, and certain polymers such as polymers containing very hydrophobic chemical groups such as silicone moieties and certain multivalent carbon soaps. The hydrophobic substance may be amorphous or crystalline and preferably essentially dispersible in the coating solvent when a solvent is used in which case it should not contribute significantly to the solution viscosity.

Aluminum salts of such acids, for example, aluminum oleates, aluminum stearates, aluminum dimerates, are also useful. Also, the hydrophobic material may be one or more polycarboxylic acids having a ratio of from 10 to 22 carbon atoms per carboxyl group are useful. Blends of these acids and/or sales are also useful.

Suitable inert flake materials include metal flake, mineral flake, crosslinked organic polymer, etc. Especially suitable are aluminum flake, talc, graphite, and ground mica.

Aluminum flake is produced by ball-milling the aluminum in a liquid medium in the presence of a lubricant such as stearic acid. It is available commercially from Alcon Metal Powders, Division of Alcon Aluminum Corporation. Sizes of the flake are generally less than about 100 microns, preferably about 1-60 microns. Talc particle sizes are generally within the range of 0.5-40 microns.

In the practice of this invention, the polymeric material may conveniently be dissolved in a suitable organic solvent which would be physiologically acceptable in the event there are residues upon evaporation of the solvent, as hereinbefore described. The hydrophobic substance is blended in the solution, wherein the polymeric substance is a continuous matrix and the additives are dispersed therein. The coating solution may be applied by various well known means such as, for example, brushing, dipping, spraying, fluidized bed, etc.

A sample of poly(2-methyl-5-vinylpyridine/styrene, 80/20) is dissolved in acetone and a portion of the flake material/hydrophobic substance/acetone dispersion or a dry mixture of flake material/hydrophobic substance is added to it with stirring. The dispersion is vigorously mixed for about 40 minutes. A small amount of water (less than 8%) may be added to the dispersion to minimize the electrostatic charges during the coating process.

An air-suspension coater is used for spray coating nutrient particles containing methionine, glucose, lysine, or other active ingredients. The typical coating temperatures are 50° C. and 32° C. for inlet and outlet air, respectively. In a typical coating operation, heated air at 0.7 m$^3$/min. at 1 kg/cm$^2$ is admitted to the chamber of the coater to cause the nutrient particles to circulate. The coating dispersion is pumped by a precision pump at a rate of °mL/min and atomized through the nozzle by compressed air at about 0.15 m$^3$/min. and 3 kg/cm$^2$ continuously. The product is in the form of pellets encapsulated with pigmented polymeric coating.

The coating weight is determined by dispersing and rinsing one gram of coated pellets with 50 mL acetone for several times until coatings were dissolved. The weight loss from coated pellets is measured to calculate the percent coating weight.

The performance of the coated pellets is evaluated by simulated in vitro rumen protection and abomasal release tests.

The protection test is done by agitating one gram of coated pellets in sodium acetate buffer at pH 5.4 for 24 hrs. in a 37° C. water bath. The release test is done by extracting one gram of pellets in sodium citrate buffer at pH 2.9 for 1 hr. in a 37° C. water bath. The supernatants taken from different media are centrifuged to remove undissolved pellets and other insoluble materials. Methionine and chloride ion concentration in the supernatants from coated methionine and lysine.HCl pellets, respectively, are determined by a X-ray fluorescence method. Glucose concentrations in the supernatants are determined by either a gravimetric method or a colorimetric method. The percent protection is calculated from the difference of the initial amount of active ingredient in the coated pellets and the amount of active ingredients released to the media.

The examples which follow are submitted for a better understanding of the invention. While the examples are based on in vitro tests, the in vitro experiments shown in the examples simulate conditions existing in ruminants thereby permitting the study of coated pellets without the use of live animals. It has been determined by actual in vivo tests that the testing of pellets in the aqueous media used in the examples, simulating the environmental conditions of the rumen and abomasum with respect to temperature, pH, etc., provide reliable data concerning the protection offered by the coatings in the rumen, and releasability of the coatings in the abomasum. Nutrients such as amino acids and proteins which may be used in the core material are known to be beneficial to ruminants when positioned in the intestinal tract downstream from the rumen.

Generally, pellets are prepared from the nutrients indicated to a size of between about 10 and 18 sieve size. The nutrients are mixed with conventional additives such as microcrystalline cellulose, binders, inert consistency adjusting substances such as water, etc. The pellets are formed by a conventional pelletizer, dried, sieved, and coated using a coater as described herein. Upon information of an imperforate coating on the pellets, they are tested for resistance to pH conditions resembling those of the rumen and abomasum by agitating in buffer solutions of pH 2.9 for 0.5 hours and 5.4 for 24 hours. Recovery and protection figures cited for active core ingredients herein contain in them all materials of the original coated pellet that are not completely dissolved in the pH 2.9 buffer, including any undissolved active ingredient in the original core.

EXAMPLE 1

Methionine cores (−12/+16 sieve size, U.S. standard) are coated with a coating formulation composed of poly(2-methyl-5-vinylpyridine/styrene, 80/20) (2M5VP/ST)/talc/aluminum/calcium stearate (31.5/38.1/25.4/5.0, by wt.). Talc, aluminum flake, and calcium stearate are ball-milled at ~40% weight per volume (w/v) in acetone and then mixed with the polymer solution to make a 5% solids coating dope. Pellets are coated as described in the coating operation. Protection values for pellets coated with the surface modified pigment formulations show improvement over the control pellets without ball-milling treatment. It requires only 8.5% coating wt. of ballmilled flake material to provide 90% methionine protection, whereas, it takes 13% coating wt. for the control pellets to reach the same value.

EXAMPLE 2

Methionine core (−12/+16 sieve size) are coated with a coating formulation composed of 2M5VP/ST/talc/aluminum/stearic acid (31.5/38.1/25.4/5.0, by wt.). Talc, aluminum flake, and stearic acid are ball-milled at 40% w/v in acetone and then mixed with the polymer solution to make a 5% solid coating dope. Pellets are coated as described in the coating operation. The protection and efficiency of the ball-mill-treated coating show improvement over the untreated control at all coating levels.

EXAMPLE 3

Methionine cores (−12/+16 sieve size) are coated with a coating formulation composed of 2M5VP/ST/talc/stearic acid (31.5/65/3.5). Talc and stearic acid are ball-milled in acetone, dried, and redispersed in the polymer solution in preparing the coating dope. Results show that the methionine protection of coated pellets with treated coatings is higher than the protection values of coated pellets without ball-milling treatments. Release of the methionine is not affected by the ball-milling treatment.

EXAMPLE 4

Glucose cores (−10/+12 sieve size) are coated with a coating formulation composed of 2M5VP/ST/talc/stearic acid (31.5/63.6/4.9). Talc and stearic acid are ball-milled in acetone, dried and redispersed in the polymer solution in preparing the coating dope. Glucose protection is 95% at pH 5.4 for pellets coated with 14% coating, and the release is completed at pH 2.9 in 1 hr. The protection values are comparable with the values for pellets coated with a coating of 2M5VP/ST/talc/aluminum/stearic acid, 31.5/39/26/3.5.

EXAMPLE 5

Glucose pellets (−12/+14 sieve size) are coated with a series of coating formulations composed of 31.5% 2M5VP/ST, 38.1% talc, 25.4% aluminum flake, and 5% stearic acid. Talc, aluminum, stearic acid are ball-milled in acetone, dried and redispersed in the polymer solution in preparing the coating dope. In another preparation, talc and aluminum, without stearic acid, are ball-milled and then dried and redispersed in a polymer solution.

At 10% coating weight, the respective protection values for various coatings are summarized in the following table. The coating composition is 2M5VP/styrene, talc, aluminum flake and stearic acid respectively in the proportions shown. Components in brackets are subjected to ball-mill treatment.

| Coating Composition | % Protection |
| --- | --- |
| 31.5 [38.1/24.4 6] | 88 |
| 31.5 [38.1/24.4] 6 | 87 |
| 31.5 38.1/24.4 6 (Control) | 51 |
| 31.5 [41.1/26.4] 1 | 77 |
| 31.5 41.1/26.4 1 (Control) | 41 |

Coatings with ball-mill treatment show significantly higher protection values than controls.

EXAMPLE 6

Lysine.HCl/methionine (8/1) cores (−12/+16 sieve size) are coated with a formulation composed of 2M5VP/ST/talc/aluminum/stearic acid (31.5/31.75/-31.75/5). Talc, aluminum flake, and stearic acid are ball-milled in acetone and directly dispersed in the polymer solution in preparing the coating dopes with two levels of total solid contents. Results show that protection values for coated pellets with ball-mill-treated coatings are higher than for the controls. The protection values for pellets coated with the treated coating at 10% solids are even higher than the respective values for the control coating at 6% solids. These results clearly demonstrate that treatment of flake material with hydrophobic substances by ball milling improves the coating efficiency. Thus, ball-milling of flake material and hydrophobic substance allows the coating to be performed at a higher dope solid content level and provides as good protection as using the dilute coating dopes.

Unless otherwise specified, the compositions in which quantities are given (e.g., 31.5/38.1/24.4/6), indicate the percent by weight of the total weight of the coating composition of polymeric material, talc, aluminum flake and flake material, respectively.

Unless otherwise specified, all ratios, percentages, etc., are by weight.

The invention has been described in detail with particular reference to preferred embodiments thereof, but it will be understood that variations and modifications can be effected within the spirit and scope of the invention.

We claim:

1. Method of preparing a composition adapted for use in coating pellets orally administrable to a ruminant which protects the core material in the rumen and releases it in the abomasum, said composition comprising
    (a) from about 16 to about 87% based on the total composition weight of a film-forming polymeric material comprising a polymer, copolymer or mixture thereof, said polymeric material having basic amino groups the nitrogen content of which constitutes between about 2 and about 14% by weight, of the polymeric material,
    (b) from about 0.5 to about 32%, based on the total composition weight of a hydrophobic material dispersed in said polymeric material selected from the group consisting of waxes, resins, polymers, fatty acids having from 12 to 32 carbon atoms, aluminum salts of fatty acids having from 12 to 32 carbon atoms and polyfunctional carboxylic acids having a ratio of from 10 to 22 carbon atoms per carboxyl group, and
    (c) from about 7 to about 80%, based on the total composition weight, of a physiologically acceptable flake material dispersed in said polymeric material, said method comprising first mixing said hydrophobic material and said flake material, causing the particles of flake material to come into rubbing contact with said hydrophobic material so that the surface of the particles of flake material become hydrophobic and subsequently blending the resulting mixture of hydrophobic material and flake material with said polymeric material to form said composition.

2. Method according to claim 1 wherein the flake material and hydrophobic material are ball-milled.

3. Method according to claim 1 wherein the duration of said rubbing contact is from about 2 to about 28 hours.

* * * * *